US012609203B2

(12) United States Patent
Rencher et al.

(10) Patent No.:  US 12,609,203 B2
(45) Date of Patent:  Apr. 21, 2026

(54) METHOD, APPARATUS, AND SYSTEM FOR IDENTIFYING THE HEALTH STATUS OF A PERSON

(71) Applicant: THE BOEING COMPANY, Chicago, IL (US)

(72) Inventors: Robert J. Rencher, Normandy Park, WA (US); David Matthew Yager, Seattle, WA (US); Roland Nelson Freeman, Bellevue, WA (US); Rahul C. Thakkar, Leesburg, VA (US); Sumant Hattikudur, Renton, WA (US); Guijun Wang, Issaquah, WA (US); David Wayne Nelson, Bellevue, WA (US)

(73) Assignee: The Boeing Company, Arlington, VA (US)

( * ) Notice: Subject to any disclaimer, the term of this patent is extended or adjusted under 35 U.S.C. 154(b) by 790 days.

(21) Appl. No.: 17/540,110

(22) Filed: Dec. 1, 2021

(65) Prior Publication Data

US 2022/0181033 A1      Jun. 9, 2022

Related U.S. Application Data

(60) Provisional application No. 63/121,008, filed on Dec. 3, 2020.

(51) Int. Cl.
*G16H 50/30* (2018.01)
(52) U.S. Cl.
CPC ................................... *G16H 50/30* (2018.01)

(58) Field of Classification Search
CPC ...................................................... G16H 50/30
See application file for complete search history.

(56) References Cited

U.S. PATENT DOCUMENTS

| | | | |
|---|---|---|---|
| 2014/0245787 A1* | 9/2014 | Proud .................... | G16H 40/67 |
| | | | 63/1.13 |
| 2014/0372154 A1* | 12/2014 | Scott ...................... | G06Q 50/40 |
| | | | 705/5 |
| 2020/0367810 A1* | 11/2020 | Shouldice ............ | A61B 5/4818 |

(Continued)

OTHER PUBLICATIONS

Lenhardt, Rainer et al., "Estimation of Mean Body Temperature from Mean Skin and Core Temperature," Anesthesiology, 105:1117-1121, (2006).

*Primary Examiner* — Jay M. Patel
(74) *Attorney, Agent, or Firm* — Harrity & Harrity, LLP

(57)                ABSTRACT

Provided herein is a method, apparatus, and system for identifying a health status of an individual, by using a health challenge of the individual to gather vital sign information to generate a health status of the individual. Method for identifying health status include: generating a non-persistent identifier for a user; receiving an indication of an initiation of a health challenge for the user associated with the non-persistent identifier; receiving, responsive to the health challenge, an indication of at least one vital sign of the user; determining, from the at least one vital sign, a health status of the user; and providing an indication of the health status of the user and the associated non-persistent identifier, where the health status includes a binary indication of health of the user, and where the health status is used to permit or deny a service to the user.

20 Claims, 3 Drawing Sheets

(56)          References Cited

U.S. PATENT DOCUMENTS

| | | | |
|---|---|---|---|
| 2020/0388287 A1* | 12/2020 | Anushiravani | ...... G06N 3/0475 |
| 2021/0065916 A1* | 3/2021 | Wiener | .................. G16H 40/67 |
| 2021/0286864 A1* | 9/2021 | Burke | ..................... G06F 21/32 |
| 2022/0005567 A1* | 1/2022 | Smith | ..................... G16H 50/20 |
| 2022/0020455 A1* | 1/2022 | Cauley, III | ........ B01L 3/502715 |

* cited by examiner

METHOD, APPARATUS, AND SYSTEM FOR IDENTIFYING THE HEALTH STATUS OF A PERSON

CROSS-REFERENCE TO RELATED APPLICATIONS

This application claims benefit of U.S. Provisional Application No. 63/121,008, filed Dec. 3, 2020, the entire contents of which are incorporated herein by reference.

TECHNOLOGICAL FIELD

An example embodiment of the present disclosure relates to a method, apparatus, and system for identifying a health status of an individual, and more particularly, to using a health challenge of an individual to gather vital sign information to generate a health status of the individual.

BACKGROUND

Communicable diseases and illnesses have always presented challenges to populations. While many communicable diseases are relatively difficult to spread or have a relatively low mortality rate, some communicable diseases are easily spread and have a relatively high mortality rate. The combination of a disease being highly contagious and having a relatively high mortality rate can result in a global pandemic. Further, such a disease affects all aspects of life. One aspect of life that is significantly affected by a widespread pandemic is the ability to gather with other people. Even when the pandemic subsides or the disease is cured, people are often risk averse and will alter their behaviors, sometimes permanently.

The gathering of groups of people is a necessary factor in a variety of aspects of everyday life. Commercial airline travel is adversely affected by a general reluctance of a population to gather. To restore confidence in the gathering of people, individuals must feel comfortable and believe that those who may carry some form of communicable disease are not out in public potentially spreading said disease.

BRIEF SUMMARY

Embodiments of the present disclosure provide a method, apparatus, and system for identifying a health status of an individual, and more particularly, to using a health challenge of an individual to gather vital sign information to generate a health status of the individual. Embodiments provided herein include a method for identifying health status including: generating a non-persistent identifier for a user; receiving an indication of an initiation of a health challenge for the user associated with the non-persistent identifier; receiving, responsive to the health challenge, an indication of at least one vital sign of the user; determining, from the at least one vital sign, a health status of the user; and providing an indication of the health status of the user and the associated non-persistent identifier, where the health status includes a binary indication of health of the user, and where the health status is used to permit or deny a service to the user.

According to an example embodiment, the non-persistent identifier for the user includes an identifier to be used to identify the user only until the user reaches a predetermined destination. According to an example embodiment, the non-persistent identifier for the user includes an identifier to be used to identify the user for a predetermined time limit. The initiation of the health challenge for the user associated with the non-persistent identifier is performed in some embodiments in response to the user entering a predetermined location. The initiation of the health challenge for the user associated with the non-persistent identifier is performed, in some embodiments, in response to a request from a service provider, where the service provider permits or denies the service to the user in response to the health challenge. The initiation of the health challenge for the user associated with the non-persistent identifier is performed, in some embodiments, in response to a received broadcast request. The at least one vital sign includes, in some embodiments, a blood oxygen level, a heart rate, and/or a temperature of the user. The blood oxygen level, heart rate, and/or temperature of the user are received from a wearable device worn by the user. According to some embodiments, determining, from the at least one vital sign, a health status, is performed based on a baseline value for the at least one vital sign previously established for the user.

Embodiments provided herein include an apparatus for identifying health status including: a sensor for sensing at least one vital sign of a user; and processing circuitry configured to: generate a non-persistent identifier for the user; receive an indication of an initiation of a health challenge for the user associated with the non-persistent identifier; receive, responsive to the health challenge, an indication of at least one vital sign of the user from the sensor; determine, from the at least one vital sign, a health status of the user; and provide an indication of the health status and the associated non-persistent identifier, where the health status includes a binary indication of health of the user, and where the health status is used to permit or deny a service to the user. According to some embodiments, the non-persistent identifier for the user includes an identifier to be used to identify the user only until the user reaches a predefined destination. According to some embodiments, the non-persistent identifier for the user includes an identifier to be used to identify the user for a predetermined time limit.

The initiation of the health challenge for the user associated with the non-persistent identifier is performed, in some embodiments, in response to the user entering a predetermined location. The initiation of the health challenge for the user associated with the non-persistent identifier is performed, in some embodiments, in response to a request from a service provider, where the service provider permits or denies the service to the user in response to the health challenge. The initiation of the health challenge for the user associated with the non-persistent identifier is performed, in some embodiments, in response to a received broadcast request. The at least one vital sign includes, in some embodiments, at least one of a blood oxygen level, a heart rate, and/or a temperature of the user. The at least one of the blood oxygen level, the heart rate, or the temperature of the user is received, in some embodiments, from a wearable device worn by the user. Determining, from the at least one vital sign, a health status, is performed in some embodiments based on a baseline value for the at least one vital sign previously established for the user.

Embodiments provided herein may include a computer program product including at least one non-transitory computer-readable storage medium having computer-executable program code portions stored therein, the computer-executable program code portions including program code instructions configured to: generate a non-persistent identifier for a user; receive an indication of an initiation of a health challenge for the user associated with the non-persistent identifier; receive, responsive to the health challenge, an indication of at least one vital sign of the user from the sensor; determine, from the at least one vital sign, a health status; and provide an indication of the health status and the associated non-persistent identifier to a service provider, where the health status includes a binary indication of health of the user, and where the health status is used to permit or deny a service to the user. The initiation of the health challenge for the user associated with the non-persistent identifier is performed, in some embodiments, in response to a request from the service provider, where the service provider permits or denies the service to the user in response to the health challenge.

DETAILED DESCRIPTION

Figure 1:
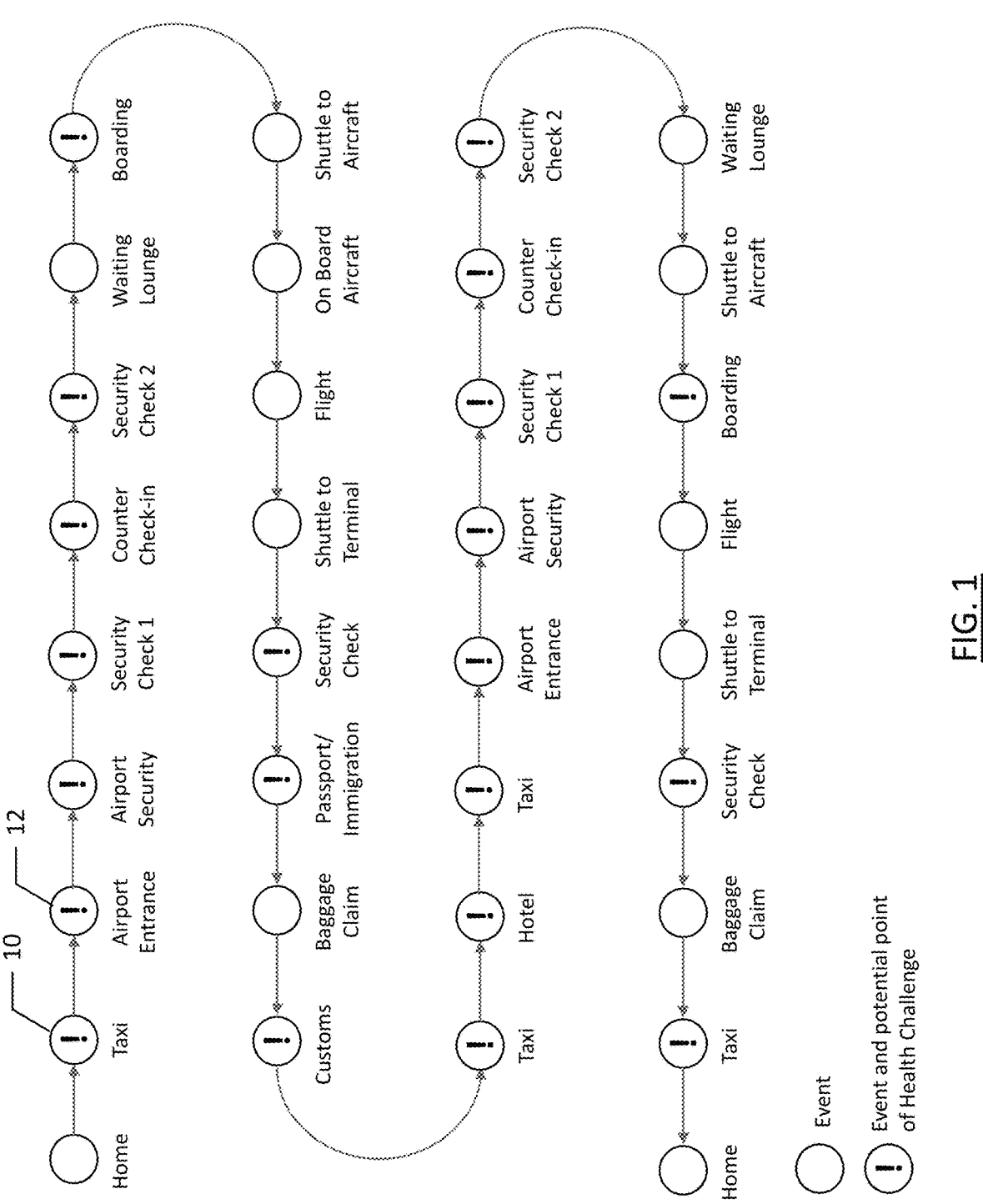
FIG. 1 illustrates an example sequence of events where certain events may be used to trigger a Health Challenge according to an embodiment of the present disclosure.

Some example embodiments of the present disclosure will now be described more fully hereinafter with reference to the accompanying drawings, in which some, but not all embodiments of the present disclosure are shown. Indeed, various embodiments of the disclosure may be embodied in many different forms and should not be construed as limited to the example embodiments set forth herein; rather, these example embodiments are provided so that this disclosure will satisfy applicable legal requirements. Like reference numerals refer to like elements throughout.

Communicable diseases including illnesses caused by viruses or bacteria are spread among a population through contact with contaminated surfaces, bodily fluids, insect bites, or through the air. Communicable diseases may have a variety of effects on a person, which may vary based on the health of the individual, the age, or any underlying conditions. The spread of communicable diseases also varies widely since some communicable diseases are exclusively spread through bodily fluid contact, while others may be airborne and much more transmissible. A communicable disease that has a relatively high mortality rate and is spread through the air can devastate a population. Further, based on the mobility of people in an era of intranational and international flight, such a disease may make its way around the world in an efficient manner resulting in a global pandemic.

During widespread disease outbreaks, epidemics, and pandemics, populations are justifiably concerned with contracting a disease. This concern affects all manners of daily life including shopping, visiting with friends and neighbors, attending school and work, and travel for work or pleasure. The concern, whether justified or not, also impacts the economy of a society when individuals reduce travel, reduce shopping, are reluctant to work in a potentially dangerous environment, or are reluctant to send their children to school for fear of contracting a disease. To mitigate the spread of disease and to improve a perceived confidence of containment of a disease, it is important to identify disease carriers and to limit their exposure to others. While some people may be aware of their illness, others may be asymptomatic or in an incubation phase of the disease or unaware of the symptoms they are experiencing. During an incubation period, a person may be unaware that a disease is developing within them but still may be contagious. Embodiments of the present disclosure provide a system and method for identifying individuals who may be ill to be able to segregate those people from a healthy population and to mitigate the spread of communicable diseases.

The commercial aviation industry, as one example, is vitally dependent on the confidence of the traveling public to operate. During disease outbreaks and even after an outbreak, public confidence may be diminished as people fear the spread of disease and contracting the disease while traveling. Based on disease outbreaks throughout the world, individuals are requiring increased confidence in their personal safety as they travel. During or after a widespread epidemic or pandemic, people will generally require a level of confidence before resuming normal activities such as travel and more specifically, travel by air. People may require a threshold level of confidence in the airline, the airport, and other participating service providers to take the appropriate precautions to protect people as they travel. Embodiments of the present disclosure provide a level of confidence that individuals can rely upon to help mitigate the spread of disease and to maintain the safety of a population. This added level of confidence can encourage people to re-join societal activities such as gatherings or traveling with commercial airlines.

Embodiments disclosed herein provide a system and method for the evaluation of health of individuals in order to identify any individuals that may carry a disease. While embodiments of the present disclosure may be implemented in a variety of settings, one particularly useful implementation is for that of commercial aviation. Airports are unique in that there is already present a degree of analysis of individuals as they traverse the airport. Security personnel along with immigration and customs enforcement personnel are already present and scrutinizing people as they arrive and depart. The airport environment provides a controlled population in a controlled setting with limited access such that employing embodiments of the present disclosure in an airport is highly desirable.

The transmission of viral and bacterial contagions on a commercial aircraft is not a new challenge to the commercial aviation industry. With the veracity of new virus strains that have decimated public confidence in institutions and businesses, such as the commercial aviation industry, to provide safe environments, public confidence must be restored. A key aspect of restoring and ensuring public confidence is the ability of the person to demonstrate that they are healthy to travel. While embodiments of the present disclosure may be implemented in various types of environments, an example is herein described with respect to commercial aviation and implemented in the environment of an airport.

Embodiments of the present disclosure include a system and method that enables an individual using "Internet of Things" or IoT enabled technology to monitor and privately demonstrate personal health using non-persistent identification to communicate their health status. The commercial aviation service providers participating in the door-to-door passenger journey may have the comparable capability to receive a non-persistent identification from an individual demonstrating personal health status. Personal health status is binary. The individual is either health or not healthy based on defined criteria which may be established, for example, by the US Centers for Disease Control (CDC).

According to an example embodiment, a mobile device application is provided for use on a mobile device of a user. The user may use this application as a form of check-in before traveling to the airport or upon arrival at the airport. The user, when requested through the application to confirm health status will demonstrate health status by use of the application. The person or a service provider initiates the creation of a non-persistent identification that will be used to temporarily identify the user and transmit their health status to the requesting service. The requesting service can be one or more and possibly all industry suppliers or generally, service providers. For example, the requesting services may include: taxi companies, rideshare companies, mass transit systems, airport access, airline check-in, security (e.g., the Transportation Security Agency, TSA), airport food services, airport lounge, gate/boarding pass, immigration, customs, etc. These services combine to form the door-to-door services for a traveler.

FIG. 1 illustrates an example sequence of events where certain events may be used to trigger a Health Challenge. The Health Challenge may be through the mobile device application and/or through other sensing equipment. An important element of embodiments described herein is voluntary use of the mobile application by the user. A user may manually enter information or a declaration of their health through entering answers to health-related questions and acknowledgement of criteria used by the mobile application. Optionally, according to some embodiments, sensors external to a user's mobile device may be used to facilitate a response to a Health Challenge. For example, a heart rate monitor which may be incorporated into a smart watch or a fitness tracker worn by a user may be used to monitor heart rate. A user's heart rate may be compared between sleeping and awake to find normal, baseline readings. Heart rate readings outside of that normal condition could indicate an infection, particularly if these deviated readings are sustained. The sleeping heart rate, which is typically relatively consistent, may be higher when a person is fighting an infection. The heart rate of the user may be communicated to the mobile application to facilitate the Health Challenge response. The baseline for any vital sign may be established based on previously gathered vital sign information for a person. For example, if a person has a high resting heart rate, that resting heart rate may be established as the baseline value for resting heart rate, whereas the fast heart rate may otherwise raise concern.

Another sensor external to a mobile device that may be used to facilitate a response to a Health Challenge is a blood oxygen sensor. Wearables, such as fitness trackers and smart watches may be able to measure blood oxygen levels. An indication of a viral respiratory infection may manifest itself in hypoxia or low blood oxygen, which would be sensed by the blood oxygen sensor. The temperature of a user may also be evaluated to establish health. While skin temperature readings may not be entirely consistent, readings are generally two to four degrees Celsius less than the core body temperature. It is possible to identify infection-based fluctuations in skin temperature, or to use the skin temperature to supplement other sensor readings in establishing a response to a Health Challenge. Skin surface temperature may be measured by the mobile device or by an external sensor, such as a fitness tracker or smart watch, for example.

The use of the aforementioned non-invasive measurements can provide an acceptable representation of a person's health. These measurements can be prescheduled to provide a periodic health determination. The evaluation can be activated by the user in the event that an intermittent Health Challenge is required. Each Health Challenge generates a binary health indicator of healthy or not healthy.

Referring again to the chart of FIG. 1, a Health Challenge may be posed to a user at a variety of instances during travel. These may prompt a user to respond via the mobile application, or these Health Challenges may be responded to by taking readings of the user's vital measures using the non-invasive processes described above. In this manner, a user could travel, substantially uninterrupted, while having their health evaluated through Health Challenges to identify any deviations from normal, healthy readings.

Health Challenges may be posed to a user based on a variety of triggers. For example, a manual trigger may be used where the user initiates a Health Challenge themselves via the mobile application and completes the Health Challenge. Completing the Health Challenge may involve entering information such as vital sign information or completing a symptom-checking questionnaire, for example. Optionally and preferably, the Health Challenge may access vital sign information from a sensor, such as sensor 30 of the apparatus 14 of FIG. 2. The sensor(s) may include blood oxygen sensor of a wearable device, a heart monitoring sensor of a wearable device, a temperature checking sensor of a wearable or of a mobile device, etc. A manual request for a Health Challenge may occur, for example, when a user hails a taxi, and the driver may require the user to complete the Health Challenge to confirm they are healthy. The Health Challenge may be sent electronically to the taxi driver or a taxi service provider, such as using the communications interface 26. Optionally, a Health Challenge may be posed to a user by the taxi driver or taxi service provider when the user requests the taxi. In requesting the taxi, whether via a mobile application, by text, or by phone, the user may be prompted to conduct a Health Challenge to verify health status before the taxi is dispatched. In the process flow of events of FIG. 1, this event with a potential point of a Health Challenge is illustrated at 10.

Manual Health Challenge requests may be performed at other points in the process flow of events of FIG. 1, such as at a security point or when boarding a plane, for example. While manual Health Challenge requests may be performed, location-based triggers may also be used to prompt a Health Challenge for a user. If a user is traveling by commercial air, such as in the process flow of events of FIG. 1, the user may be prompted for a Health Challenge upon arrival at the airport. FIG. 1 illustrates this event with the potential point of a Health Challenge at 12. The airport, or portions thereof (e.g., entrances) may be geo-fenced such that upon entry into the geo-fenced area or upon entering a predetermined location, the user may be prompted for a Health Challenge to confirm their health status. Location-based Health Challenges may be used for a variety of events, including any event that takes place within a fixed location.

Health Challenge requests may optionally be broadcast by a service provider. For example, in an embodiment of an airport, the airport may broadcast the Health Challenge to apparatuses as they approach or enter the airport to solicit a response.

Embodiments described herein may raise privacy concerns among users. However, embodiments may mitigate these concerns through the use of the non-persistent user identifier. This temporary identifier may not be retained such that re-identification of a user is not possible. The temporary identifier may be valid for a finite period of time, or during a travel session of a user. For example, the temporary identifier may be valid from when a user departs an origin until the user arrives at a destination, and subsequently expunged as the mobile application successfully completed its role in the travel process.

While a mobile application may be used as described above to present Health Challenges that a user must satisfy, embodiments may include the use of sensors in an environment for identifying potential health-related issues of passengers. One such type of sensor includes an infrared temperature scanning sensor to scan the body temperature of people proceeding through an area. An example of how such sensors could be implemented includes use of the infrared temperature scanning sensors at a security checkpoint in an airport. As people presently are individually sent through scanning booths or metal detectors, a temperature sensor could be implemented seamlessly. Further, implementation in a security checkpoint would allow sequestration of an individual for further health analysis if the temperature scan revealed any potential health concerns.

While security checkpoints may be relatively ideal situations for implementing temperature scanning sensors, other situations may include temperature scanning sensors employed in walkways, such as causeways, sky bridges, or concourses where people must travel to reach their destination. To implement temperature scanning in such an environment, embodiments could employ personnel proximate the temperature scanning sensors, where upon identifying an individual having a temperature that raises health concerns, the personnel can be presented with an image of the individual for the personnel to make contact with the individual and to discretely sequester them for further health screening.

Infrared temperature checks can be readily deployed given current technology. Future embodiments may include remote, non-contact heart rate sensors and blood oxygen sensors that can be implemented in a manner similar to that of the infrared temperature sensors. A health screening sensor suite can evaluate the vital signs of a user and provide the analysis to appropriate personnel in order to have any individuals with health concerns further screened to determine if they are ill, and if so, is the illness a communicable disease that would put other people at risk.

Example embodiments as described herein may be implemented in a variety of scenarios where the health status of a person may be of interest before providing a service to a user or to allow a user to gain entrance or access a building or area. One example of such a scenario may include an event, where the event organizers want to ensure all who attend have a healthy health status. If the event is at a location such as a stadium, the options for requesting the Health Challenge may be many. For example, a person, when accessing their tickets on a mobile device, may be required to complete a Health Challenge. Further, the stadium could be geofenced such that any person approaching the stadium to have their tickets scanned receives an indication of initiation of a Health Challenge for them to complete. Still further, ticket booths or ticket operators may broadcast a request for or an initiation of a Health Challenge to all who approach.

Beyond commercial air travel and events, embodiments could be employed in office buildings, factories, or other places of work to ensure all who are entering the place of work have successfully completed a Health Challenge to the satisfaction of the building operator. Restaurants, retail stores, and many other entities may employ the Health Challenge strategy as described herein. The commercial air travel embodiment described above is of particular usefulness as there are many events during a journey that present opportunities for the completion of Health Challenges.

Figure 2:
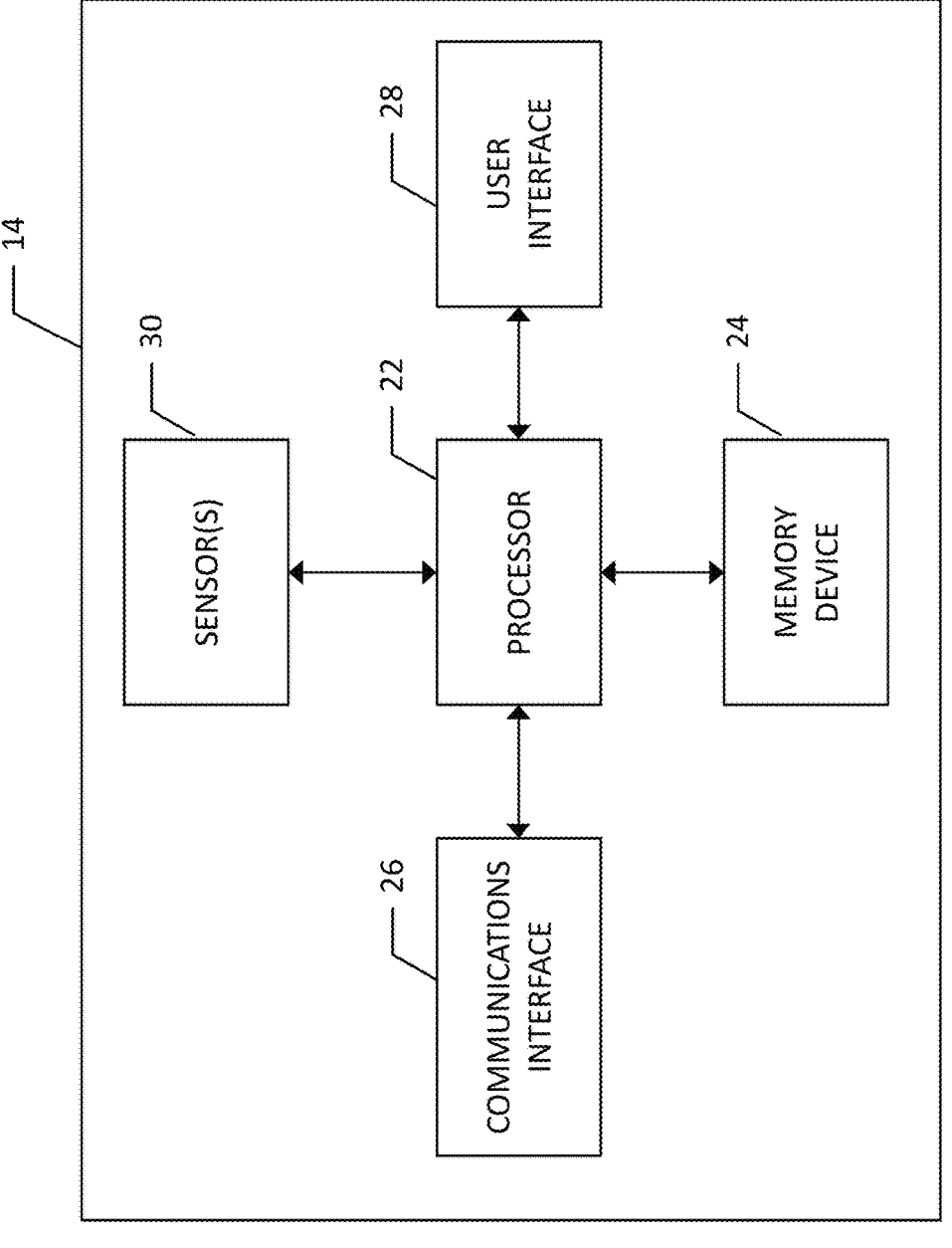
FIG. 2 is a schematic diagram of an example of an apparatus that may be implemented for use with the mobile application according to an example embodiment of the present disclosure.

FIG. 2 is a schematic diagram of an example of an apparatus 14 that may be implemented for use with the mobile application of example embodiments. The apparatus 14 may be in the form of a mobile phone, a tablet computer, a smart watch, a fitness tracker, or various other mobile devices that may facilitate at least one of operation of the mobile application or measuring vital signs of a user. The apparatus 14 may include or otherwise be in communication with a processor 22, a memory device 24, a communication interface 26 and a user interface 28. Although devices or elements are shown as being in communication with each other, hereinafter such devices or elements should be considered to be capable of being embodied within the same device or element and thus, devices or elements shown in communication should be understood to alternatively be portions of the same device or element.

In some embodiments, the processor 22 (and/or co-processors or any other processing circuitry assisting or otherwise associated with the processor) may be in communication with the memory device 24 via a bus for passing information among components of the apparatus. The memory device 24 may include, for example, one or more volatile and/or non-volatile memories. In other words, for example, the memory device 24 may be an electronic storage device (e.g., a computer readable storage medium) comprising gates configured to store data (e.g., bits) that may be retrievable by a machine (e.g., a computing device like the processor). The memory device 24 may be configured to store information, data, content, applications, instructions, or the like for enabling the apparatus 14 to carry out various functions in accordance with an example embodiment of the present disclosure. For example, the memory device 24 could be configured to buffer input data for processing by the processor 22. Additionally or alternatively, the memory device could be configured to store instructions for execution by the processor.

The processor 22 may be embodied in a number of different ways. For example, the processor 22 may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor may include one or more processing cores configured to perform independently. A multi-core processor may enable multiprocessing within a single physical package. Additionally or alternatively, the processor 22 may include one or more processors configured in tandem via the bus to enable independent execution of instructions, pipelining and/or multithreading. The processor may be embodied as a microcontroller having custom bootloader protection for the firmware from malicious modification in addition to allowing for potential firmware updates.

In an example embodiment, the processor 22 may be configured to execute instructions stored in the memory device 24 or otherwise accessible to the processor 22. Alternatively or additionally, the processor 22 may be configured to execute hard coded functionality. As such, whether configured by hardware or software methods, or by a combination thereof, the processor 22 may represent an entity (e.g., physically embodied in circuitry) capable of performing operations according to an example embodiment while configured accordingly. Thus, for example, when the processor 22 is embodied as an ASIC, FPGA or the like, the processor 22 may be specifically configured hardware for conducting the operations described herein. Alternatively, as another example, when the processor 22 is embodied as an executor of software instructions, the instructions may specifically configure the processor 22 to perform the algorithms and/or operations described herein when the instructions are executed. However, in some cases, the processor 22 may be a processor of a specific device (e.g., a smart watch) configured to employ an embodiment of the present disclosure by further configuration of the processor 22 by instructions for performing the algorithms and/or operations described herein. The processor 22 may include, among other things, a clock, an arithmetic logic unit (ALU) and logic gates configured to support operation of the processor 22. In one embodiment, the processor 22 may also include user interface circuitry configured to control at least some functions of one or more elements of the user interface 28.

The communication interface 26 may include various components, such as a device or circuitry embodied in either hardware or a combination of hardware and software that is configured to receive and/or transmit data for communicating data between a service provider and a user. The service provider may be a third party service provider that facilitates health screening of users. Optionally, a facility, such as an airport, may operate as its own service provider. In this regard, the communication interface 26 may include, for example, an antenna (or multiple antennas) and supporting hardware and/or software for enabling communications wirelessly. Additionally or alternatively, the communication interface 26 may include the circuitry for interacting with the antenna(s) to cause transmission of signals via the antenna(s) or to handle receipt of signals received via the antenna(s). For example, the communications interface 26 may be configured to communicate wirelessly such as via Wi-Fi (e.g., vehicular Wi-Fi standard 802.11p), Bluetooth, mobile communications standards (e.g., 3G, 4G, or 5G) or other wireless communications techniques. In some instances, the communication interface 26 may alternatively or also support wired communication, which may communicate with a separate transmitting device (not shown). As such, for example, the communication interface 26 may include a communication modem and/or other hardware/software for supporting communication via cable, digital subscriber line (DSL), universal serial bus (USB) or other mechanisms. For example, the communication interface 26 may be configured to communicate via wired communication with other components of a computing device.

The user interface 28 may be in communication with the processor 22, such as the user interface circuitry, to receive an indication of a user input and/or to provide an audible, visual, mechanical, or other output to a user. As such, the user interface 28 may include, for example, one or more buttons, light-emitting diodes (LEDs), a display, a speaker, and/or other input/output mechanisms. The user interface 28 may also be in communication with the memory device 24 and/or the communication interface 26, such as via a bus. The user interface 28 may include an interface with which a user may enter responses to Health Challenges and/or to acknowledge and approve access by a service provider to receive sensor data relating to vital signs of the user.

Figure 3:
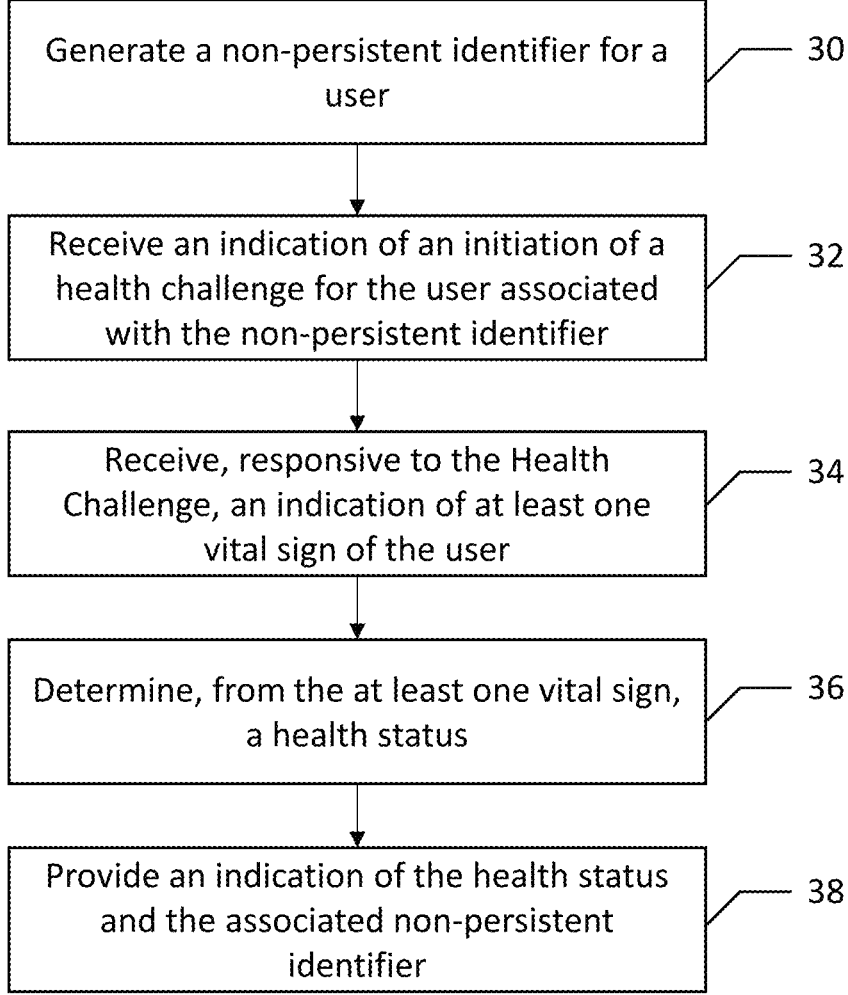
FIG. 3 is a flowchart of a method for identifying a health status of an individual according to an example embodiment of the present disclosure.

FIG. 3 illustrates a flowchart of a method according to an example embodiment of the disclosure. It will be understood that each block of the flowchart, and combinations of blocks in the flowchart, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by the memory device 24 of an apparatus employing an example embodiment and executed by the processor 22 of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowcharts support combinations of means for performing the specified functions and combinations of operations for performing the specified functions for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

According to the flow chart of FIG. 3, a non-persistent identifier for a user is generated at 30. That non-persistent identifier is to identify the user only for a finite period which may be a temporally based period or event based period, whereby the period may end at the conclusion of an elapsed time or the conclusion of an event, such as a traveling event. At 32, an indication of an initiation of a Health Challenge for the user associated with the non-persistent identifier is received. Responsive to the Health Challenge, an indication of at least one vital sign of the user is received at 34. Based on the at least one vital sign, a health status is determined at 36. This health status is a binary indication as to whether the user is able to access a service, enter an area, or continue with travel, for example. An indication of the health status and the associated non-persistent identifier are provided at 38. The indication may be provided, for example to a service provider to enable the service provider to decide whether to permit or deny service to the user.

In an example embodiment, an apparatus for performing the method of FIG. 3 above may comprise a processor (e.g., the processor 22) configured to perform some or each of the operations (30-38) described above. The processor may, for example, be configured to perform the operations (30-38) by performing hardware implemented logical functions, executing stored instructions, or executing algorithms for performing each of the operations. Alternatively, the apparatus may comprise means for performing each of the operations described above. In this regard, according to an example embodiment, examples of means for performing operations 30-38 may comprise, for example, the processor 22 and/or a device or circuit for executing instructions or executing an algorithm for processing information as described above.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these embodiments pertain having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for identifying health status comprising:

receiving, by a device, a request from a service provider to confirm a health status of a user based on the device entering a geo-fenced location at an airport;

generating, by the device, a non-persistent identifier for the user when requested through an application associated with the device to confirm the health status of the user, wherein the non-persistent identifier for the user comprises an identifier to be used to identify the user until a conclusion of an airplane traveling event;

receiving, by the device, an indication of an initiation of a health challenge for the user;

receiving, by the device and responsive to the health challenge, an indication of at least one vital sign of the user;

determining, by the device and from the at least one vital sign, the health status of the user; and providing, by the device, an indication of the health status of the user and the non-persistent identifier to the service provider, wherein the health status of the user comprises a binary indication of health of the user, and wherein the health status of the user is broadcast by the device to permit or deny a service to the user, wherein the service includes entry past a security service.

2. The method of claim 1, wherein the request is a broadcast request.

3. The method of claim 1, wherein the at least one vital sign comprises at least one of a blood oxygen level, a heart rate, or a temperature of the user.

4. The method of claim 3, wherein the at least one of the blood oxygen level, the heart rate, or the temperature of the user is received from a wearable device worn by the user.

5. The method of claim 1, wherein determining, from the at least one vital sign, the health status, is performed based on a baseline value for the at least one vital sign.

6. An apparatus for identifying health status comprising:

a sensor for sensing at least one vital sign of a user; and processing circuitry configured to:

receive a request from a service provider to confirm a health status of the user based on a device entering a geo-fenced location;

generate a non-persistent identifier for the user when requested through an application associated with the apparatus to confirm the health status of the user, wherein the non-persistent identifier for the user comprises an identifier to be used to identify the user only until a conclusion of an event;

receive an indication of an initiation of a health challenge for the user;

receive, responsive to the health challenge, an indication of at least one vital sign of the user from the sensor;

determine, from the at least one vital sign, the health status of the user; and provide an indication of the health status of the user and the non-persistent identifier to the service provider, wherein the health status of the user comprises a binary indication of health of the user, and wherein the health status of the user is broadcast by the apparatus to permit or deny a service to the user, wherein the service includes entry past a security checkpoint.

7. The apparatus of claim 6, wherein the non-persistent identifier for the user comprises an identifier to be used to identify the user for a predetermined time limit.

8. The apparatus of claim 6, wherein the request is a broadcast request.

9. The apparatus of claim 6, wherein the at least one vital sign comprises at least one of a blood oxygen level, a heart rate, or a temperature of the user.

10. The apparatus of claim 9, wherein the at least one of the blood oxygen level, the heart rate, or the temperature of the user is received from a wearable device worn by the user.

11. The apparatus of claim 6, wherein the health status of the user is performed based on a baseline value for the at least one vital sign.

12. A computer program product comprising at least one non-transitory computer-readable storage medium having computer-executable program code portions stored therein, the computer-executable program code portions comprising program code instructions configured to:

receive a request from a service provider to confirm a health status of a user based on a device entering a geo-fenced location at an airport;

generate a non-persistent identifier for the user when requested through an application on a mobile device to confirm the health status of the user, wherein the non-persistent identifier for the user comprises an identifier to be used to identify the user only until a conclusion of an airplane traveling event;

receive an indication of an initiation of a health challenge for the user;

receive, responsive to the health challenge, an indication of at least one vital sign of the user from a sensor;

determine, from the at least one vital sign, the health status of the user; and provide the indication of the health status and the non-persistent identifier to a service provider, wherein the health status comprises a binary indication of health of the user, and wherein the health status is broadcast by the mobile device to permit or deny a service to the user, wherein the service includes entry past a security checkpoint.

13. The method of claim 1, further comprising:

permitting the user to enter based on receiving sensor data relating to at least one other vital sign of the user.

14. The computer program product of claim 12, wherein the request is a broadcast request.

15. The computer program product of claim 12, wherein the at least one vital sign comprises a blood oxygen level of the user.

16. The method of claim 1, wherein the non-persistent identifier for the user comprises an identifier to be used to identify the user for a predetermined time limit.

17. The method of claim 1, wherein receiving the indication of at least one vital sign of the user comprises:

receiving, from a sensor, the indication of the at least one vital sign of the user.

18. The apparatus of claim 6, wherein the sensor is one or more of:

a fitness tracker, or a smart watch.

19. The computer program product of claim 12, wherein the health status is performed based on a baseline value for the at least one vital sign.

20. The computer program product of claim 12, wherein the non-persistent identifier for the user comprises an identifier to be used to identify the user for a predetermined time limit.

\* \* \* \* \*